United States Patent
Shin et al.

(10) Patent No.: US 9,995,738 B2
(45) Date of Patent: Jun. 12, 2018

(54) APPARATUS AND METHOD FOR DETECTING AND COUNTING RARE CELLS IN BLOOD

(71) Applicant: Korea University Research and Business Foundation, Seoul (KR)

(72) Inventors: Sehyun Shin, Seoul (KR); Chang-Soo Han, Seoul (KR); Dae Ho Jang, Gyeonggi-do (KR)

(73) Assignee: Korea University Research and Business Foundation, Seoul (KR)

( * ) Notice: Subject to any disclaimer, the term of this patent is extended or adjusted under 35 U.S.C. 154(b) by 368 days.

(21) Appl. No.: 14/775,860

(22) PCT Filed: Mar. 13, 2014

(86) PCT No.: PCT/KR2014/002086
§ 371 (c)(1),
(2) Date: Sep. 14, 2015

(87) PCT Pub. No.: WO2014/142559
PCT Pub. Date: Sep. 18, 2014

(65) Prior Publication Data
US 2016/0025714 A1 Jan. 28, 2016

(30) Foreign Application Priority Data

Mar. 13, 2013 (KR) .......................... 10-2013-0026810
Mar. 12, 2014 (KR) .......................... 10-2014-0029109

(51) Int. Cl.
*G01N 33/53* (2006.01)
*G01N 33/58* (2006.01)
(Continued)

(52) U.S. Cl.
CPC ......... *G01N 33/5302* (2013.01); *G01N 21/00* (2013.01); *G01N 33/574* (2013.01); *G01N 33/582* (2013.01)

(58) Field of Classification Search
None
See application file for complete search history.

(56) References Cited

U.S. PATENT DOCUMENTS

2003/0129676 A1    7/2003  Terstappen et al.
2005/0048599 A1*   3/2005  Goldberg ................. B82Y 5/00
                                                     435/34
(Continued)

FOREIGN PATENT DOCUMENTS

JP    2002-514739 A    5/2002
JP    2011-133377 A    7/2011
(Continued)

*Primary Examiner* — Rebecca L Martinez
(74) *Attorney, Agent, or Firm* — Fox Rothschild LLP

(57) ABSTRACT

The present invention relates to an apparatus and method for detecting and enumerating a rare cell in blood. The apparatus comprises a sample collector configured to collect a blood sample and receive a complex in which a target antibody and a marker are coupled; a measuring kit connected to the sample collector in such a way that a mixture of the blood sample and the complex is injected into the measuring kit, thereby individually trapping a blood cell; and a detector configured to detect and enumerate the rare cell having an antigen-antibody reaction with the target antibody among the blood cell trapped in the measuring kit.

16 Claims, 5 Drawing Sheets

(51) Int. Cl.
*G01N 21/00* (2006.01)
*G01N 33/574* (2006.01)

(56) References Cited

U.S. PATENT DOCUMENTS

| | | | |
|---|---|---|---|
| 2006/0147901 A1* | 7/2006 | Jan | G01N 33/54326 435/4 |
| 2009/0286264 A1* | 11/2009 | Scholtens | G01N 33/54326 435/7.21 |
| 2010/0178690 A1 | 7/2010 | Kim et al. | |

FOREIGN PATENT DOCUMENTS

| | | |
|---|---|---|
| KR | 10-0399475 B1 | 9/2003 |
| KR | 2009-0087594 A | 8/2009 |
| KR | 2009-0131588 A | 12/2009 |
| KR | 2011-0013485 A | 2/2011 |

* cited by examiner

[FIG. 1]
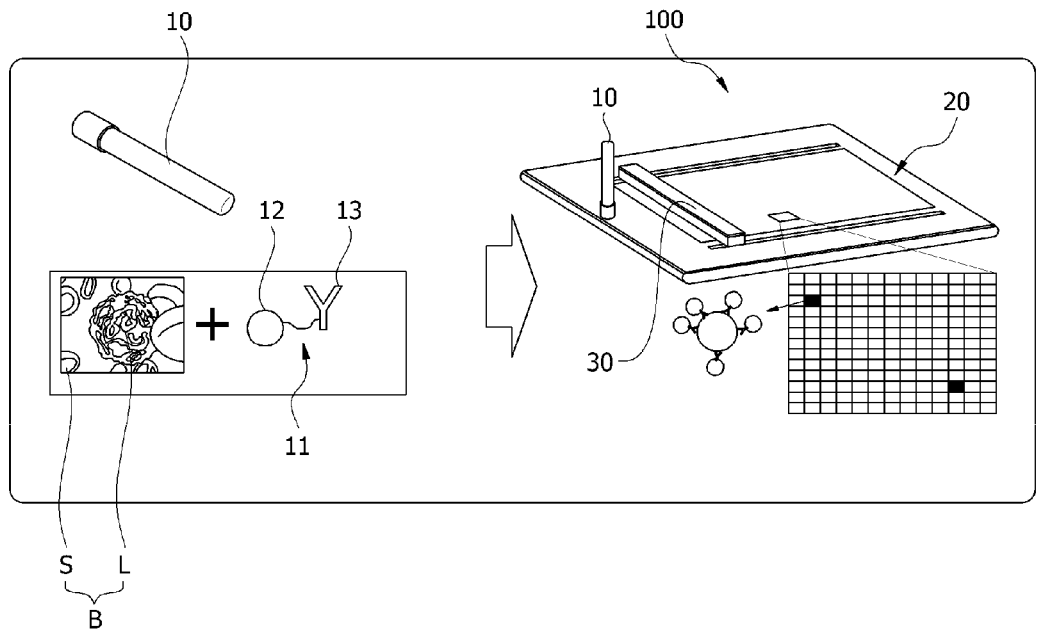
[FIG. 2]
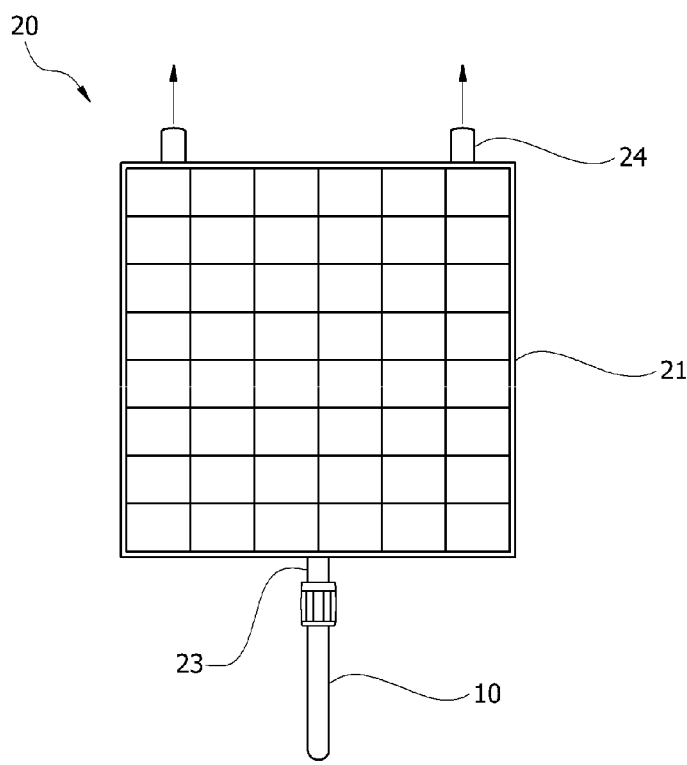

【FIG. 3】
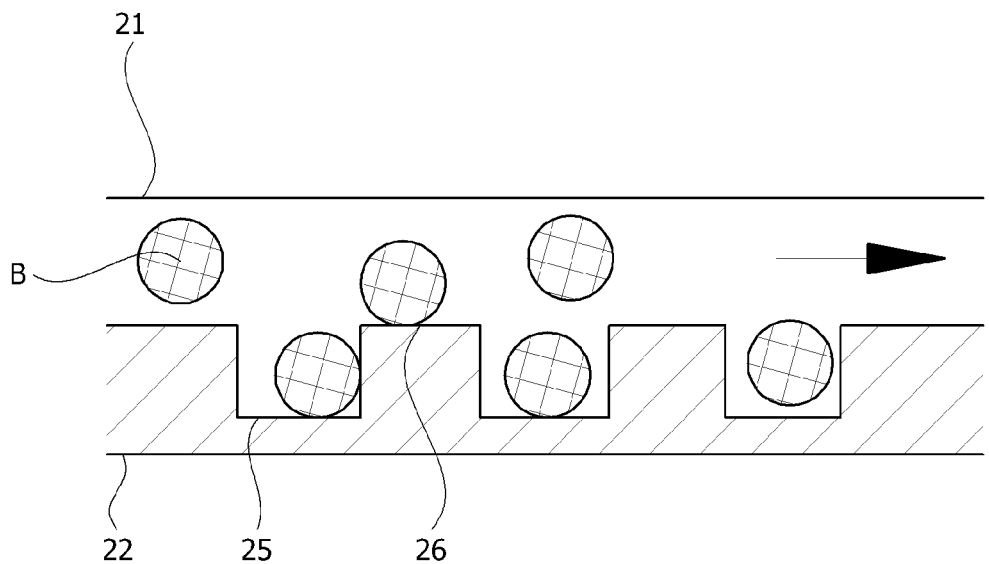
【FIG. 4】
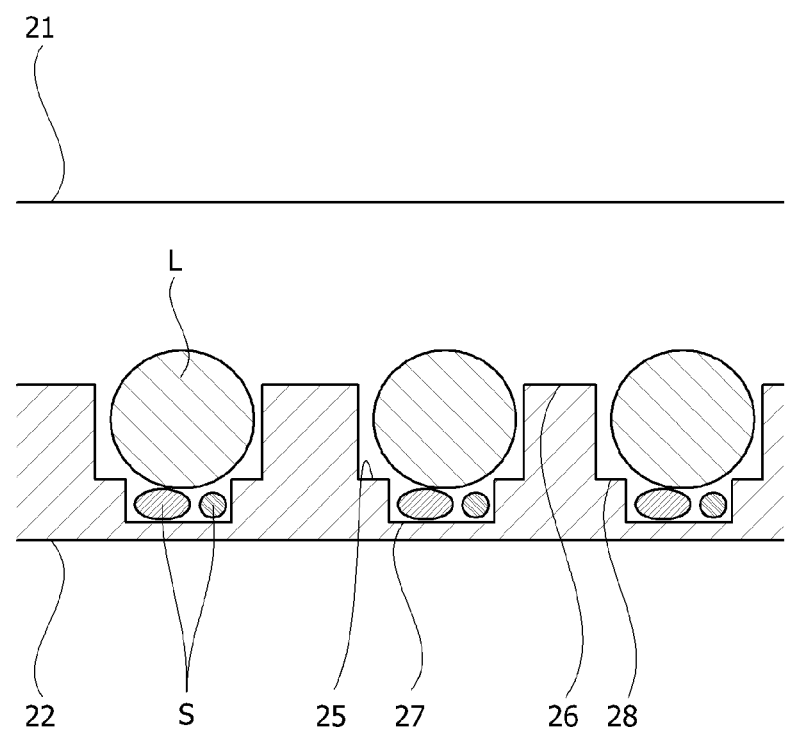

[FIG. 5]
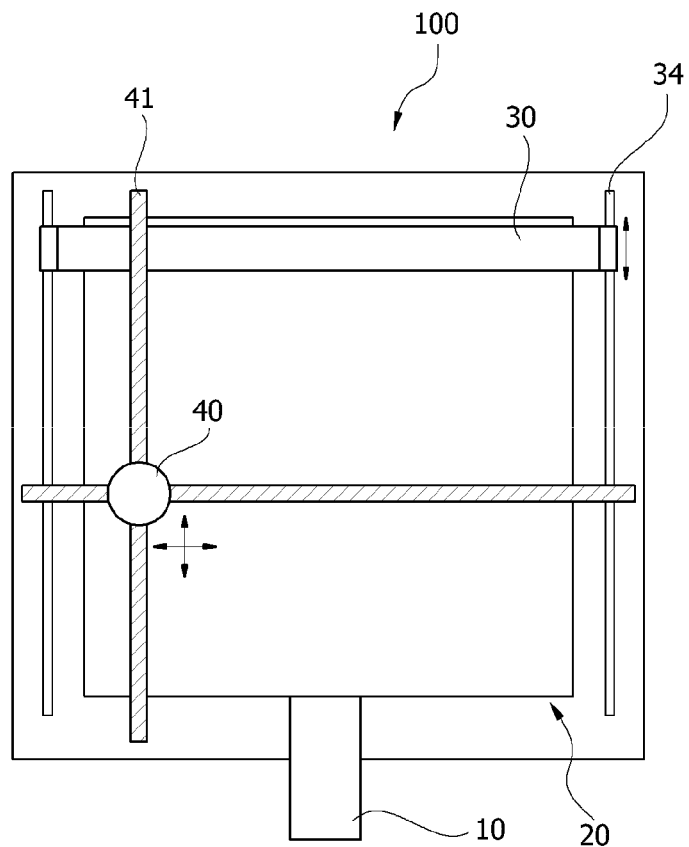
[FIG. 6]
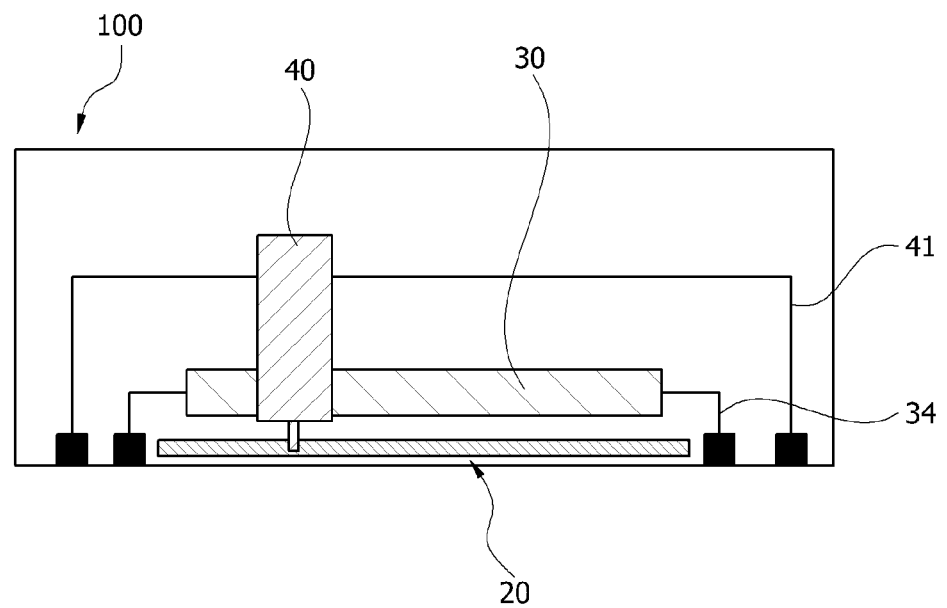

[FIG. 7]
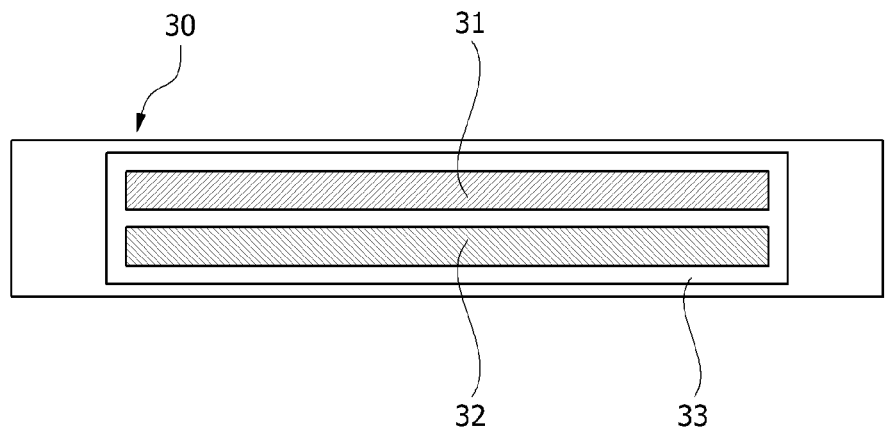
[FIG. 8]
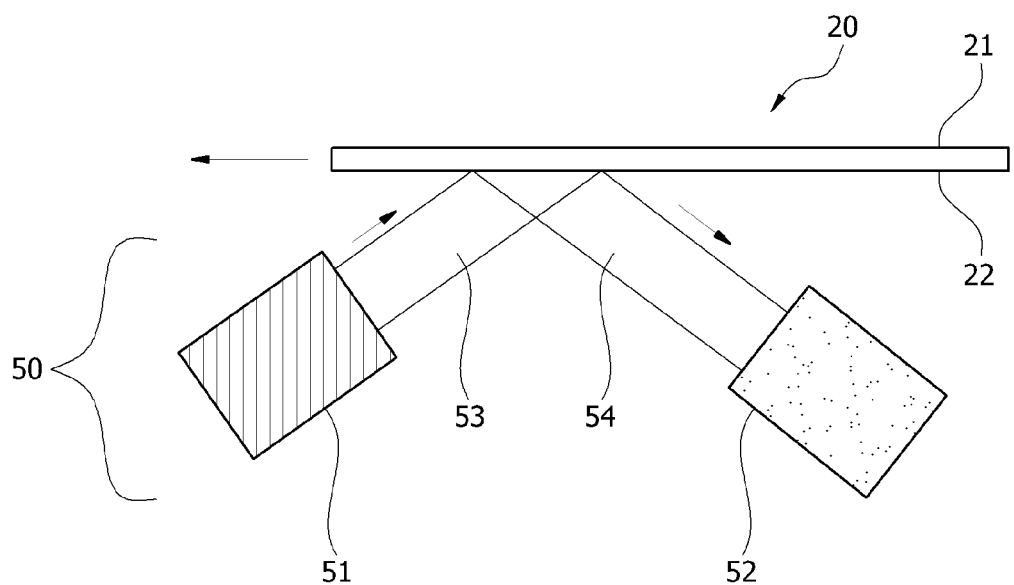

[FIG. 9]
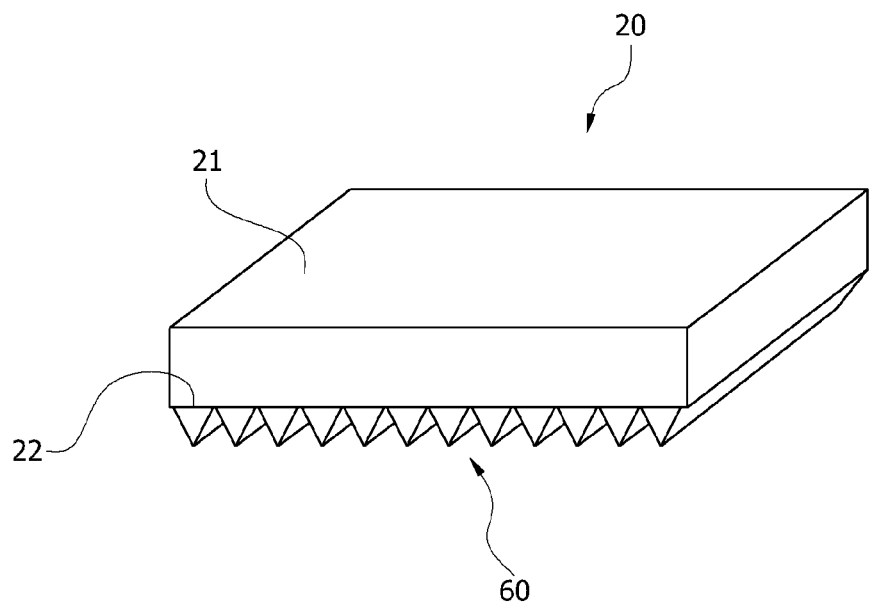

APPARATUS AND METHOD FOR DETECTING AND COUNTING RARE CELLS IN BLOOD

CROSS REFERENCE TO RELATED APPLICATIONS

This application is the U.S. National Phase of International Application No. PCT/KR2014/002086, filed Mar. 13, 2014which claims priority of Korean Application Nos. 10-2013-0026810,filed Mar. 13, 2013 and 10-2014-0029109, filed Mar. 12, 2014, the disclosures of which are all incorporated herein by reference.

TECHNICAL FIELD

The present invention relates to an apparatus and method for detecting and enumerating a rare cell in blood, and more particularly, to an apparatus and method for detecting and enumerating a rare cell in blood such as a circulating endothelial cell (CEC) using a simple complex in which a target antibody and a marker are coupled, and plates with a micro gap.

BACKGROUND ART

In whole blood, it is known that there are a small minority of cells that can play an important role in a metastasis of a disease or can be used as a biomarker, which are called rare cells, compared to conventionally known blood cells such as red blood cells, white blood cells, and platelets.

Circulating tumor cells (CTC) are representative of rare cells, and it is known that one or two CTCs exist in several billions of blood cells. When many CTCs are found, it can be a very critical clue for determining the possibility of diagnosing cancer through a blood test, and thus various blood test methods using the CTCs are being developed.

Recent clinical papers and related techniques show that CECs can be used as a biomarker in an early diagnosis of cardiovascular diseases such as a heart attack, and therefore CTC-like or related techniques are being rapidly developed.

For example, in "Characterization of circulating endothelial cells in acute myocardial infarction," from Science Translational Medicine which was published on March, 2012, it was disclosed that a cardiovascular diseases group had about five times the CECs of a healthy group, and it was reported that an increase in the number of such CECs over a predetermined number may lead to a diagnosis of a risk of a heart attack within 2 weeks.

The cells such as CTCs or CECs are very difficult to isolate or detect by a common technique since very few exist, and they are very critical rare cells involved in two major causes of human death, for example, cancer and cardiovascular disease. This technique for the detection of such cells may be difficult, but in that it can test for cancers and cardiovascular diseases by only providing a small amount of blood (7.5 ml) from the patient's perspective, it is a very innovative technique that has a market waiting for it.

The currently known method of detecting CTCs or CECs is a method of detecting rare cells using an antigen-antibody reaction, which has very high selectivity. That is, a surface of a nano particle having magnetic property is coated with antibodies that can be attached in response to antigens of specific rare cells, and mixed with a blood sample by stirring, thereby the nano particles are attached to the specific rare cells which exist in the blood. Then, they are tightly fixed using a magnetic force, and washed to remove remaining cells, thereby isolating only the specific rare cells. The isolated rare cells may be verified by staining under a microscope, and then cells in each sample may be enumerated.

However, such conventional methods require separate processes such as a pretreatment and a post treatment, and such processes take a very long time. Also, to handle such processes, a skillful examiner is definitely necessary, and therefore, it is very difficult to use the conventional methods in a clinical setting. Accordingly, in order to be rapidly used in the clinical setting, examination should be simple and fast, and in order to easily perform examination by medical personnel, a quantified and objectified apparatus and method for detection are required.

DISCLOSURE

Technical Problem

An object of the present invention is to provide an apparatus and method for rapidly and precisely detecting and enumerating a small minority of rare cell from a predetermined amount of blood.

Technical Solution

In order to accomplish the object, the present invention provides an apparatus for detecting and enumerating a rare cell in blood, comprising: a sample collector configured to collect a blood sample and receive a complex in which a target antibody and a marker are coupled; a measuring kit connected to the sample collector in such a way that a mixture of the blood sample and the complex is injected into the measuring kit, thereby individually trapping a blood cell; and a detector configured to detect and enumerate the rare cell having an antigen-antibody reaction with the target antibody among the blood cell trapped in the measuring kit.

In the present invention, the target antibody may specifically recognize the rare cell in the blood and bind to the rare cell.

In the present invention, the marker may include at least one selected from a fluorescent material; a quantum dot; a micro bead in which the quantum dot is integrated; and a metal nano particle.

In the present invention, the blood sample collected in the sample collector may be stirred with a dispersion solution of the complex.

In the present invention, the measuring kit may include two plates with a micro-scale gap, and allow the blood sample to be moved by capillary action. In the present invention, the plates may be manufactured in a rigid plate-type structure or a flexible film-type structure.

In the present invention, the measuring kit may include an inlet formed at one end of the measuring kit and a capillary tube formed at the other end of the measuring kit, the blood sample may be injected into the inlet, the capillary tube may have an opening which is in communication with the outside, and air may pass through the opening.

In the present invention, the opening of the capillary tube may be connected to a fluidization driving mechanism, and allow the blood sample to be injected into the measuring kit and fluidized in the measuring kit.

In the present invention, at least one of the two plates may include a concave-convex part to individually trap the blood cell.

In the present invention, the concave-convex part may have a step in a stair shape, a small cell may be trapped in a lower portion of the concave-convex part, and a large cell may be trapped in an upper portion of the concave-convex part.

In the present invention, the detector may be a fluorescence scanner configured to detect a position and a number of the blood cell that emits a light, and the fluorescence scanner may include a light source configured to excite at least one selected from the fluorescent material, the quantum dot, and the micro beads in which the quantum dot is integrated; an image sensor configured to detect excited fluorescence; and a fluorescence filter through which a specific wavelength range of light passes.

In the present invention, the light source may include at least one selected from a mercury lamp, a laser diode (LD) and a laser light-emitting diode (LED). In the present invention, the image sensor may include at least one selected from a photo diode array, a charge coupled device (CCD) array, and a complementary metal oxide semiconductor (CMOS) array.

In the present invention, the image sensor may have a zoom lens to obtain an optically enlarged image.

In the present invention, the light source and the image sensor may be installed in such a way that the light source and the image sensor may be sequentially joined.

In the present invention, the detector may be a surface plasmon resonance imaging scanner configured to detect a position and a number of the blood cell having a surface plasmon resonance phenomenon, and the surface plasmon resonance imaging scanner may include at least one selected from an optical device capable of generating the surface plasmon resonance phenomenon of the metal nano particle, a micro-scale prism array and a nano-scale grating array.

In the present invention, the surface plasmon resonance imaging scanner may include a light source configured to emit a parallel light to the measuring kit; and a camera configured to detect the light reflected from the measuring kit.

In the present invention, the measuring kit may be integrated with the micro-scale prism array or the nano-scale grating array.

The apparatus of the present invention may further comprise a moving rail connected to the detector, and configured to guide movement of the detector for scanning of the measuring kit; a moving collector configured to collect a sample after detection; and a biaxial moving rail connected to the moving collector, and configured to guide movement of the moving collector.

Furthermore, the present invention provides a method of detecting and enumerating a rare cell in blood using the above-mentioned apparatus. The method of the present invention comprises collecting the blood sample by the sample collector; mixing and stirring the collected blood sample and the complex in which the target antibody and the marker are coupled; injecting the mixture of the blood sample and the complex into the measuring kit, and individually trapping the blood cell; and detecting and enumerating the rare cell having the antigen-antibody reaction with the target antibody among the blood cell trapped in the measuring kit, using the detector.

Advantageous Effects

According to the present invention, a rare cell can be rapidly, easily and simply detected and enumerated by mixing a mixture of a blood sample and a complex in which a target antibody and a marker are coupled in a disposable blood collection tube, injecting the mixture into plates of a measuring kit, and counting the number of a light-emitting micro trap. The objectified and standardized detection and enumeration are possible even by general medical personnel using a simple operating method. Particularly, due to a short time spent on one examination, mass examination is also possible.

DESCRIPTION OF DRAWINGS

FIG. 1 schematically illustrates an apparatus and method for detecting and enumerating a rare cell in blood according to the present invention.

FIG. 2 is a plan view of a measuring kit according to the present invention.

FIG. 3 is a cross-sectional view illustrating a mechanism in which cells are trapped in the measuring kit having a concave-convex structure according to the present invention.

FIG. 4 is a cross-sectional view illustrating another mechanism in which cells are trapped in the measuring kit having a stair-shaped concave-convex structure according to the present invention.

FIG. 5 is a plan view of the apparatus according to the present invention.

FIG. 6 is a front view of the apparatus according to the present invention.

FIG. 7 is a diagram of a fluorescence scanner as a detector according to the present invention.

FIG. 8 is a diagram of a surface plasmon resonance imaging scanner as the detector according to the present invention.

FIG. 9 is a perspective view illustrating that a micro-scale prism array or a nano-scale grating array used in a surface plasmon resonance imaging method is integrated with the measuring kit according to the present invention.

MODES OF THE INVENTION

Hereinafter, the present invention will be described with reference to the accompanying drawings.

FIG. 1 schematically illustrates an apparatus and method for detecting and enumerating a rare cell in blood according to the present invention, and the apparatus 100 according to the present invention may be a diagnostic system for the rare cell, which may include a sample collector 10, a measuring kit 20, and a detector 30.

The sample collector 10 serves to collect a blood sample, and to receive a complex 11. That is, the blood sample is loaded to the sample collector 10.

The sample collector 10 may be formed in a tube shape, and include a plug. Preferably, the sample collector 10 may have the structure of a 7.5 ml blood collection tube, which is commonly and widely used.

The blood sample may include a plurality of blood cells B, which are broadly classified into two groups: a small cell S such as a red blood cell; and a large cell L such as a white blood cell and the rare cell.

The complex 11 may include a marker 12 and a target antibody 13, which are coupled to each other. The marker 12 and the target antibody 13 may be chemically coupled by a linker, or physically coupled. There is no particular limitation to the linker, and thus a conventional linker, for example a peptide linker, a hydrazine linker or a disulfide linker may be used.

The complex 11 may be provided in the form of a solution containing the complex 11, and preferably a dispersion solution prepared by dispersing the complex 11 in a dispersion medium. For example, the dispersion solution of the complex may include the complex 11 as a dispersoid, water as the dispersion medium, and a surfactant as a dispersing agent.

As the marker 12, at least one selected from 1) a fluorescent material, 2) a quantum dot, 3) a micro bead in which the quantum dot is integrated and 4) a metal nano particle may be used.

As the fluorescent material, a conventional fluorescent material may be used without particular limitation, and for example fluorescein, isothiocyanate, rhodamine, phycoerythrin, phycocyanin, allophycocyanin, phthaldehyde, fluorescamine, etc. may be used. The size of the fluorescent material may be, but is not particularly limited to, for example 1 to 900 nm, preferably 10 to 500 nm, and more preferably 30 to 300 nm.

The quantum dot may include a core particle and a ligand binding to a surface of the core particle. An example of a material for forming the core particle may be II-VI group compound semiconductor nanocrystal such as CdS, CdSe, CdTe, ZnS, ZnSe, ZnTe, HgS, HgSe, HgTe; III-V group compound semiconductor nanocrystal such as GaN, GaP, GaAs, InP, InAs; or a mixture thereof. The core particle may have a core/shell structure, and each of the core and shell of the core particle may include the above-described compounds. The above-described compounds may be included in the core or shell alone or in combination of at least two thereof. For example, the core particle may have a CdSe—ZnS (core/shell) structure in which CdSe is contained as the core and ZnS is contained as the shell. The ligand can prevent extinction caused by instant agglomeration of adjacent core particles. In addition, the ligand is bonded to the core particle such that the core particle can have hydrophobicity. An example of the ligand may be an amine-based compound or carboxylic acid compound, which has an alkyl group having 6 to 30 carbon atoms. Another example of the ligand may be an amine-based compound or carboxylic acid compound, which has an alkenyl group having 6 to 30 carbon atoms. The size of the quantum dot may be, but is not particularly limited to, for example 1 to 900 nm, preferably 10 to 500 nm, and more preferably 30 to 300 nm.

The micro bead in which the quantum dot is integrated may have a capsule structure surrounding a quantum dot aggregate formed by integrating a plurality of quantum dots. The capsule may be manufactured using a gelatin, a cellulose-based compound, etc. The size of the micro bead may be, but is not particularly limited to, for example 0.1 to 900 μm, preferably 0.5 to 500 μm, and more preferably 1 to 100 μm.

As a metal for constituting the metal nano particle, any of conventional metals, for example gold, silver, bronze, iron, platinum, tungsten, titanium, tin, nickel, chromium, cobalt, zinc, iridium, etc. may be used without particular limitation. Also, a metal oxide, a metal salt or an alloy may be used. The size of the metal nano particle may be, but is not particularly limited to, for example 1 to 900 nm, preferably 10 to 500 nm, and more preferably 30 to 300 nm.

The target antibody 13 may be an antibody capable of specifically recognizing the rare cell in blood such as CTC, CEC, etc. and binding thereto. For example, an Anti-EpCAM antibody may be used.

A predetermined amount of the blood sample may be collected in the sample collector 10, and then stirred with the dispersion solution of the complex present in the sample collector 10 for mixing. The stirring may be manually performed by shaking by hand, or automatically performed using a stirrer. The order of mixing the blood sample with the dispersion solution of the complex is not particularly limited, and the blood sample may be put into the sample collector 10 first, or the dispersion solution of the complex may be put into the sample collector 10 first. During stirring, when a specific rare cell in blood is present, a large amount of the complexes 11 in which the marker 12 and the target antibody 13 are coupled may be attached around a cell membrane of the rare cell through an antigen-antibody reaction.

On the lower right side of FIG. 1, there is a scanning image illustrating cell counting, wherein a black spot in a plurality of lattices represents a hybridized rare cell (RC) to which the complex binds.

FIG. 2 is a plan view of the measuring kit according to the present invention, and the measuring kit 20 may include plates 21 and 22, an inlet 23, a capillary tube 24, and a concave-convex structure 25, 26, 27 and 28.

The measuring kit 20 serves to individually trap the blood cell. The measuring kit 20 may be connected to the sample collector 10 in such a way that the mixture of the blood sample and the complex 11 is injected into the measuring kit 20. To this end, the inlet 23 into which the blood sample is injected may be formed at one end of the measuring kit 20. The inlet 23 may be formed, for example, in a needle shape, or have a needle structure. For example, when the sample collector 10 is stood upside down, and then the plug of the sample collector 10 is put on the needle-shaped inlet 23 or the needle structure of the inlet 23, the sample collector 10 and the measuring kit 20 are connected to each other, and therefore the mixture of the blood sample and the complex stirred in the sample collector 10 may be injected into the measuring kit 20.

The measuring kit 20 may be formed in a microfluidic sheet structure for cell spreading. Preferably, the measuring kit 20 may include two plates 21 and 22 having a microscale gap, and may be capable of moving the blood sample by capillary action. However, the present invention is not limited thereto, and the measuring kit 20 may be formed in one plate structure, or in a structure having three or more plates. The gap between the two plates 21 and 22 may be, for example, 1 to 500 μm, preferably 5 to 100 μm, and more preferably 10 to 50 μm.

The plates 21 and 22 may be manufactured in a rigid plate-type structure or flexible film-type structure. The plates 21 and 22 may be formed of metal, plastic, glass, ceramic, etc. and may be preferably transparent to facilitate detection. The thickness of the plates 21 and 22 may be, for example, 1 μm to 10 mm, preferably 10 μm to 5 mm, and more preferably 50 μm to 3 mm.

When the two plates 21 and 22 are disposed parallel to each other at a regular interval, edge portions between the two plates 21 and 22, that is, the right and left sides and the front and back sides between the two plates 21 and 22 may be open, and an opened portion may be sealed with a sealing material. Alternatively, the measuring kit 20 may be manufactured in a very thin hexahedron shaped integrated structure without the opened portion. Of course, the inlet 23 and the capillary tube 24 may be separately formed.

The capillary tube 24 may allow the mixture of the blood sample and the complex to easily flow between the two plates 21 and 22 of the measuring kit 20. To this end, the capillary tube 24 may be formed at the other end of the measuring kit 20, for example, at the opposite side of the inlet 23. The capillary tube 24 may include an opening which is in communication with the outside, and air may pass through the opening. The opening may be formed, for example, at the terminal end of the capillary tube 24. The diameter of the capillary tube 24 may be, for example 0.01 to 100 μm, preferably 0.1 to 50 μm, and more preferably 0.5 to 20 μm such that only the air can pass through.

A fluidization driving mechanism may be connected to the opening at the terminal end of the capillary tube 24, thereby injecting the blood sample into the measuring kit 20 at an appropriate rate, and allowing the blood sample to be fluidized in the measuring kit 20. The fluidization driving mechanism may include, for example, a vacuum pump. For example, when the vacuum pump is operated to create a vacuum in the measuring kit 20 and then is stopped to operate, the blood sample may flow forward and then backward (counterflow), and may be evenly spread on the whole. Also, an injection rate and fluidization rate of the blood sample may be adjusted depending on a pressure of the vacuum pump.

FIG. 3 is a cross-sectional view illustrating a mechanism in which cells are trapped in the measuring kit having a concave-convex structure according to the present invention, a concave and convex part 25 and 26 may be included in at least one of the two plates 21 and 22 to individually trap the blood cell B. In FIG. 3, the concave and convex part 25 and 26 is formed in the lower plate 22, but the present invention is not limited thereto, and thus the concave and convex part 25 and 26 may be formed in the upper plate 21. Alternatively, the concave and convex part 25 and 26 may be formed in both of the plates 21 and 22.

The concave-convex part 25 and 26 may be composed of a concave part 25 and a convex part 26, and preferably may be form in a fine microstructure. A number of the concave and convex part 25 and 26 is not particularly limited, but varies depending on a size of the measuring kit 20. The number of the concave and convex part 25 and 26 is preferably 10 or more, and more preferably 100 or more. Even numbers of 10,000 or more, 100,000 or more, 1,000,000 or more are possible.

Each of the width, length, and height (depth) of the concave and convex part 25 and 26 is for example 0.1 to 200 μm, preferably 0.5 to 70 μm, and more preferably 1 to 30 μm.

In FIG. 3, the arrow marks the direction of movement of the blood sample, and it can be confirmed that the blood cell B is trapped in the concave part 25.

Meanwhile, the fluidization driving mechanism, in order to individually trap the blood cell B in a trap of the concave and convex part 25 and 26, may repeatedly induce a forward flow or backward flow of the blood sample between the two plates 21 and 22, and thereby one cell B can be trapped in one of the concave and convex part 25 and 26.

FIG. 4 is a cross-sectional view illustrating another mechanism in which cells are trapped in the measuring kit having a stair-shaped concave-convex structure according to the present invention, a stair-shaped step may be formed in the concave and convex part 25, 26, 27, and 28, and thus a small cell S may be trapped in a lower portion of the concave and convex part, and a large cell L may be trapped in an upper portion of the concave and convex part.

The stair-shaped concave-convex structure may be, as shown in FIG. 4, a structure in which a small concave part 27 is further formed on a lower portion of a large concave part 25. Also, a small convex part 28 may be formed by carving both sides of an upper portion of a large convex part 26, or by protruding from both sides of a lower portion of the large convex part 26.

As described above, the concave and convex part 25, 26, 27, and 28 may be formed in a stair shape having a step difference, and thus, as shown in FIG. 3, the small cell S such as a red blood cell may be trapped in the small concave part 27, and the large cell L such as a white blood cell and the rare cell may be trapped in the large concave part 25, which is placed directly over the small concave part 27.

Also, the concave and convex part 25, 26, 27, 28 may be formed to have an optimal depth (height) and width so that the escape of the trapped cell S and L caused by external fluidization can be prevented. Since the size of the red blood cell may be approximately 1 to 8 μm and the size of the white blood cell may be approximately 12 to 25 μm, the width and depth of the small concave part 27 may be approximately 1 to 10 μm and the width and depth of the large concave part 25 may be approximately 11 to 30 μm. As a result, the blood sample may be injected into the measuring kit 20, and each cell B may be trapped in each micro trap structure.

Meanwhile, the measuring kit 20 may be installed on a support of the apparatus 100 to count the number of the cell which emit a light in response to the complex 11 or have a surface plasmon resonance phenomenon among the cell captured in the concave and convex part 25, 26, 27, and 28.

FIG. 5 is a plan view of the apparatus according to the present invention, and FIG. 6 is a front view of the apparatus, and the apparatus 100 may include a moving rail 34, a moving collector 40, and a biaxial moving rail 41, in addition to the sample collector 10, the measuring kit 20 and the detector 30.

The detector 30 may serve to detect and enumerate the rare cell having an antigen-antibody reaction with the target antibody 13 among the blood cell B trapped in the measuring kit 20. The detector 30 may detect the position and number of the blood cell by an optical method. The detector 30 may include, for example, a high accuracy CCD sensor array, and detect the position and the number of a light-emitting cell by scanning the measuring kit 20. The detector 30 may be a fluorescence scanner or a surface plasmon resonance imaging scanner depending on a type of the marker 12, and will be described later.

The moving rail 34 serves to guide the movement of the detector 30 for scanning of the measuring kit 20. To this end, one end of the moving rail 34 may be installed on the support of the apparatus 100, and the other end of the moving rail 34 may be connected to the detector 30. The detector 30 may be moved up and down on FIG. 5 along the moving rail 34. The detector 30 may include a wheel or roller to be moved along the moving rail 34. The moving rail 34 may be fixed and may not be moved. The movement of the detector 30 may be manual movement by hand or automatic movement by a motor.

The moving collector 40 serves to collect a sample after detection. The moving collector 40 may be formed, for example, in a syringe form. When using the syringe form, the sample may be collected by piercing the upper plate 21 of the measuring kit 20. The moving collector 40 may be manually moved by hand or automatically moved by the motor.

The biaxial moving rail 41 serves to guide the movement of the moving collector 40. The biaxial moving rail 41 may consist of a vertical rail and a horizontal rail as shown in FIG. 5, and the moving collector 40 may be installed at an intersecting point of the two rails. The moving collector 40 may be moved up and down and right and left on FIG. 5 along the biaxial moving rail 41. The biaxial moving rail 41 may be not fixed to the support of the apparatus 100 and may be installed to be self-moving, and may be moved along with the moving collector 40.

When the scanning of the detector 30 is finished, the moving collector 40 may be moved to a target position along the biaxial moving rail 41 by addressing a detected position of the rare cell, and thus the rare cell can be collected. The collected sample may be used as a specimen for a secondary precision analysis.

FIG. 7 is a diagram of the fluorescence scanner as the detector according to the present invention. When the marker 12 is at least one selected from 1) the fluorescent material, 2) the quantum dot, and 3) the micro bead in which the quantum dot is integrated, the detector 30 may be constituted in the form of the fluorescence scanner.

The fluorescence scanner 30 may include a light source 31 capable of exciting at least one selected from the fluorescent material, the quantum dot, and the micro bead in which the quantum dot is integrated; an image sensor 32 capable of measuring excited fluorescence; and a fluorescence filter 33 through which a specific wavelength range of light can pass, and thus the position and the number of the light-emitting blood cell may be detected.

The light source 31 may include at least one selected from a mercury lamp, a laser diode (LD) and a laser light-emitting diode (LED).

The image sensor 32 may include at least one selected from a photo diode array, a charge coupled device (CCD) array, and a complementary metal oxide semiconductor (CMOS) array.

A zoom lens may be installed on the image sensor 32, and thus an optically enlarged image may be obtained.

The light source 31 and the image sensor 32 may be installed in such a way that the light source 31 and the image sensor 32 may be sequentially joined.

The wavelength range of light passing through the fluorescence filter 33 may be determined by a type of the fluorescent material or quantum dot used.

After the detection, the measuring kit 20 may be examined by an optical device such as a microscope, thereby confirming the morphology of cells at the location of light emission.

FIG. 8 is a diagram of the surface plasmon resonance imaging scanner as the detector according to the present invention. When the marker 12 is the metal nano particle, the detector 30 may be constituted in the form of the surface plasmon resonance imaging scanner 50.

The surface plasmon resonance imaging scanner 50 may include at least one selected from an optical device capable of generating the surface plasmon resonance phenomenon of the metal nano particle, a micro-scale prism array and a nano-scale grating array, and thus may detect the position and number of the blood cell having the surface plasmon resonance phenomenon.

The surface plasmon resonance imaging scanner 50 may include, as shown in FIG. 8, a light source 51 emitting a parallel light 53 to the measuring kit 20; and a camera 52 detecting a reflected light 54 from the measuring kit 20.

As described above, in the surface plasmon resonance imaging scanner 50, the light 54 reflected from the measuring kit 20 into which the parallel light 53 is incident may be detected by the camera 52. When a large amount of the metal nano particle is attached to the rare cell in blood and the light is incident into the cell at a specific incident angle, the light is absorbed only at the position of the cell, thereby generating a difference in the amount of reflected light from other parts of the measuring kit 20, and the detection may be accomplished using such a difference. For example, the light with a wavelength of 400 to 900 nm may be incident at an angle of 10 to 80 degrees. Preferably, the light with a wavelength of 600 to 800 nm may be incident at an angle of 30 to 70 degrees.

FIG. 9 is a perspective view illustrating that the micro-scale prism array or nano-scale grating array used in a surface plasmon resonance imaging method is integrated with the measuring kit according to the present invention, wherein the measuring kit 20 may be integrated with the micro-scale prism array 60 or nano-scale grating array in order to make a condition for the surface plasmon resonance phenomenon.

The prism array 60 or grating array may be integrated with an external surface of the measuring kit 20, and specifically integrated with the external surface of the upper plate 21 or the lower plate 22 by adhesion, welding, injection molding, extrusion molding, etc.

The shape of the prism array 60 or grating array preferably has a triangular cross-section as shown in FIG. 9, but may be a circular, oval or polygonal shape when necessary.

The size of the prism array 60 may be, for example 1 μm to 1 mm, preferably 10 to 500 μm, and more preferably 100 to 200 μm. The size of the grating array may be, for example 1 nm to 10 μm, preferably 10 nm to 3 μm, and more preferably 100 nm to 1 μm.

DESCRIPTIONS OF SYMBOLS

10: Sample collector
11: Complex
12: Marker
13: Target antibody
20: Measuring kit
21, 22: Plate
23: Inlet
24: Capillary tube
25, 26, 27, 28: Concave-convex part
30: Detector (Fluorescence scanner)
31: Light source
32: Image sensor
33: Fluorescence filter
34: Moving rail
40: Moving collector
41: Biaxial moving rail
50: Surface plasmon resonance imaging scanner
51: Light source
52: Camera
53: Parallel light
54: Reflected light
60: Prism array (grating array)
100: Apparatus for detecting and enumerating rare cell (rare cell diagnostic system)

The invention claimed is:

1. An apparatus for detecting and enumerating a rare cell in blood, comprising:
   a sample collector configured to collect a blood sample and receive a complex in which a target antibody and a marker are coupled;
   a measuring kit connected to the sample collector in such a way that a mixture of the blood sample and the complex is injected into the measuring kit, thereby individually trapping a blood cell;
   a detector configured to detect and enumerate the rare cell having an antigen-antibody reaction with the target antibody among the blood cell trapped in the measuring kit;

a moving rail connected to the detector, and configured to guide movement of the detector for scanning of the measuring kit;

a moving collector configured to collect a sample after detection; and a biaxial moving rail connected to the moving collector, and configured to guide movement of the moving collector, wherein the measuring kit includes two plates with a micro-scale gap, and allows the blood sample to be moved by capillary action, wherein at least one of the two plates includes a concave-convex part to individually trap the blood cell, and wherein the concave-convex part has a step in a stair shape, and is configured to trap a small cell in a lower portion of the concave-convex part, and a large cell in an upper portion of the concave-convex part.

2. The apparatus of claim 1, wherein the target antibody specifically recognizes the rare cell in the blood and binds to the rare cell.

3. The apparatus of claim 1, wherein the marker includes at least one selected from a fluorescent material; a quantum dot; a micro bead in which the quantum dot is integrated; and a metal nano particle.

4. The apparatus of claim 1, wherein the blood sample collected in the sample collector is stirred with a dispersion solution of the complex.

5. The apparatus of claim 1, wherein the plates are manufactured in a rigid plate-type structure or a flexible film-type structure.

6. The apparatus of claim 1, wherein the measuring kit includes an inlet formed at one end of the measuring kit and a capillary tube formed at the other end of the measuring kit, such that the blood sample is injected into the inlet, and wherein the capillary tube has an opening which is in communication with the outside, and air passes through the opening.

7. The apparatus of claim 6, wherein the opening of the capillary tube is connected to a fluidization driving mechanism, and allows the blood sample to be injected into the measuring kit and fluidized in the measuring kit.

8. The apparatus of claim 3, wherein the detector is a fluorescence scanner configured to detect a position and a number of the blood cell that emits a light, and the fluorescence scanner includes a light source configured to excite at least one marker selected from the fluorescent material, the quantum dot, and the micro beads in which the quantum dot is integrated; an image sensor configured to detect excited fluorescence; and a fluorescence filter through which a specific wavelength range of light passes.

9. The apparatus of claim 8, wherein the light source includes at least one selected from a mercury lamp, a laser diode (LD) and a laser light-emitting diode (LED).

10. The apparatus of claim 8, wherein the image sensor includes at least one selected from a photo diode array, a charge coupled device (CCD) array, and a complementary metal oxide semiconductor (CMOS) array.

11. The apparatus of claim 8, wherein the image sensor has a zoom lens to obtain an optically enlarged image.

12. The apparatus of claim 8, wherein the light source and the image sensor are installed in such a way that the light source and the image sensor are sequentially joined.

13. The apparatus of claim 3, wherein the detector is a surface plasmon resonance imaging scanner configured to detect a position and a number of the blood cell having a surface plasmon resonance phenomenon, and the surface plasmon resonance imaging scanner includes at least one selected from an optical device capable of generating the surface plasmon resonance phenomenon of the metal nano particle, a micro-scale prism array and a nano-scale grating array.

14. The apparatus of claim 13, wherein the surface plasmon resonance imaging scanner includes a light source configured to emit a parallel light to the measuring kit; and a camera configured to detect the light reflected from the measuring kit.

15. The apparatus of claim 13, wherein the measuring kit is integrated with the micro-scale prism array or the nano-scale grating array.

16. A method of detecting and enumerating a rare cell in blood using the apparatus of claim 1, the method comprising:

collecting the blood sample by the sample collector;

mixing and stirring the collected blood sample and the complex in which the target antibody and the marker are coupled;

injecting the mixture of the blood sample and the complex into the measuring kit, and individually trapping the blood cell; and detecting and enumerating the rare cell having the antigen-antibody reaction with the target antibody among the blood cell trapped in the measuring kit, using the detector.

* * * * *